US00PP32299P2

(12) United States Plant Patent
Kordes

(10) Patent No.: US PP32,299 P2
(45) Date of Patent: Oct. 13, 2020

(54) FLORIBUNDA ROSE PLANT NAMED 'KORFLOCI111'

(50) Latin Name: *Rosa hybrida*
Varietal Denomination: KORfloci111

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/602,226

(22) Filed: Sep. 3, 2019

(51) Int. Cl.
*A01H 5/02* (2018.01)
*A01H 6/74* (2018.01)

(52) U.S. Cl.
USPC ..... Plt./144

(58) Field of Classification Search
USPC ..... Plt./101, 141, 144
See application file for complete search history.

(56) References Cited

U.S. PATENT DOCUMENTS

PP17,841 P2 7/2007 Meilland

*Primary Examiner* — Susan McCormick Ewoldt
*Assistant Examiner* — Karen M Redden
(74) *Attorney, Agent, or Firm* — Panitch Schwarze Belisario & Nadel LLP

(57) ABSTRACT

A new and distinct variety of Floribunda Rose Plant, herein referred to by its cultivar name, 'KORfloci111', is provided which forms attractive, cup-like white colored blossoms. The vegetation is vigorous and the growth habit is very bushy and rounded. Attractive semi-glossy, medium-green ornamental foliage is formed. Very good disease resistance is exhibited. The new variety is particularly well suited for providing distinctive ornamentation in the landscape.

1 Drawing Sheet

Botanical/commercial classification:
Latin name—*Rosa hybrida.*
Common name—Floribunda Rose Plant.
Varietal denomination: 'KORfloci111'.

SUMMARY OF THE INVENTION

The new variety of *Rosa hybrida* Floribunda Rose Plant of the present invention was created by controlled breeding during May 2005 at Sparrieshoop, Germany by artificial pollination wherein two parents were crossed which previously had been studied in the hope that they would contribute the desired characteristics. The female parent (i.e., seed parent) of the new variety was an unnamed seedling (non-patented) resulting from a cross of the 'KORpeligo' variety (non-patented) and an unnamed seedling. The male parent (i.e., pollen parent) of the new variety was the 'KORfloci12' variety (non-patented).

The parentage can be summarized as follows:

('KORpeligo' x unnamed seedling) x 'KORfloci12'

The seeds resulting from the above pollination were sown and small plants were obtained which were physically and biologically different from each other. Selective study resulted in the identification of a single plant of the new variety.

It was found that the new Floribunda Rose Plant of the present invention possesses the following combination of characteristics:

(a) forms attractive cup-like white colored blossoms,
(b) exhibits a very bushy and rounded growth habit,
(c) forms vigorous vegetation, (d) forms attractive ornamental semi-glossy, medium green foliage, and
(e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling from the ('KORpeligo' x unnamed seedling) cross (i.e., seed parent) exhibits a light pink colored flower, which is smaller in size and has less petals per flower compared to the white colored flower of the new variety. Additionally, the 'KORfloci12' variety (i.e., pollen parent) exhibits a crimson red with a cream reverse colored flower, which has more petals per flower compared to the white colored flower of the new variety and the 'KORfloci12' variety provides a lower level of disease resistance compared to the new variety. Moreover, the new variety can be readily distinguished from non-parental related similar varieties. For example, the 'Meidelweis' variety (U.S. Plant Pat. No. 17,841) displays flowers with more petals, exhibits more fragrance, and produces a darker green foliage compared to the new variety.

The new variety has been found to undergo asexual propagation at Wasco, Calif. and Cochranville, Pa. by a number of routes such as vegetative cuttings. Asexual propagation techniques in Wasco, Calif. and Cochranville, Pa., such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORfloci111'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately two years of age and was observed at Cochranville, Pa. while growing outdoors on its own roots in a three-gallon container.

FIG. 1—illustrates a specimen of the plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a two-years-old specimen of the new variety, observed during May, while growing in a three-gallon container on its own roots at Cochranville, Pa.

Class: Floribunda Rose Plant.

Plant:

*Habit*.—Very bushy and rounded.

*Height*.—Approximately 45.0 cm on average.

*Width*.—Approximately 40.0 cm on average.

Branches:

*Stem color*.—Old wood: commonly near Green Group 143A. — young stems: commonly near Green Group 143B.

*Length*.—Main stem: approximately 45.0 cm on average. — secondary stem: approximately 16.0 cm on average.

*Diameter*.—Main stem: approximately 8.0 mm on average. — secondary stem: approximately 3.0 mm on average.

*Thorns*.—Young thorns: length is approximately 6.0 mm on average; width is approximately 4.0 mm at point of attachment on average; color is commonly near Yellow-Green Group 146C. — old thorns: length is approximately 9.0 mm on average; width is approximately 4.0 mm at point of attachment on average; color is commonly near Brown Group 200D.

Foliage:

*Young foliage*.—Upper surface color: commonly near Green Group 143B with indistinguishable venation. — under surface color: commonly near Green Group 143C with venation of near Green Group 143D.

*Old foliage*.—Upper surface color: commonly near Green Group 143A with indistinguishable venation. — under surface color: commonly near Green Group 143C with venation of near Green Group 143D.

*Petioles*.—Upper surface: texture is smooth; color is commonly near Yellow-Green Group 144A. — under surface: texture is glandular with sparse prickles; color is commonly near Yellow-Green Group 144A. — length: approximately 3.9 cm on average. — diameter: approximately 1.0 mm on average.

*Rachis*.—Color: upper and under surfaces are commonly near Yellow-Green Group 144A. — length: approximately 7.0 cm on average. — diameter: approximately 1.0 mm on average.

*Stipules*.—Length: approximately 2.0 cm on average. — width: approximately 3.0 mm on average. — margin: entire to erose. — color: upper surface is commonly near Yellow-Green Group 144A with some mixing near Greyed-Orange Group 176A particularly close to the innermost portion; lower surface is commonly near Yellow-Green Group 144A.

*Leaf margin*.—Serrate.

Leaflets:

*Number*.—3, 5, and 7.

*Shape*.—Ovate; apex is acute to acuminate; and base is cuneate.

*Leaf undulation*.—Weak.

*Venation pattern*.—Reticulate.

*Texture*.—Upper surface is smooth; under surface is smooth.

*Glossiness intensity of the upper side of the leaf*.—Moderate.

*Size*.—Terminal leaflet: length is approximately 4.5 cm on average; width is approximately 3.0 cm on average. — lower leaflets: length is approximately 3.5 cm on average; width is approximately 2.0 cm on average. — 5-Leaflet leaf: length is approximately 11.0 cm on average; width is approximately 6.5 cm on average.

Inflorescence:

*Number of flowers*.—Approximately 18 blooms on average on a plant at once.

*Number of blooms per stem*.—Commonly 1 to 5 blooms per stem on average.

*Peduncle*.—Color: commonly near Yellow-Green Group N144C. — diameter: approximately 1.0 mm on average. — length: approximately 3.5 cm on average. — surface texture: sparely echinulate.

*Sepals*.—Number: commonly 5. — upper surface color and texture: covered in short pubescence; color is commonly near Yellow-Green Group 144A. — under surface color and texture: puberulent; color is commonly near Yellow-Green Group 144B. — size: length is approximately 2.0 cm on average; width is approximately 1.0 cm on average. — shape: apex is acute to aristate; base is truncate or flat as it joins the receptacle. — margin: entire with occasional extensions on two or three sepals measuring approximately 5.0 mm in length and approximately 1.0 mm in width.

*Bud*.—Shape: ovoid. — size: length is approximately 2.5 cm on average; width is approximately 1.7 cm on average. — color when opening: commonly near White Group NN155A with blending of near Red Group 48C along outermost margin.

*Flower*.—Fragrance: very slight. — form: double, cup-like — profile: flat. — diameter: approximately 8.0 cm on average. — height: approximately 2.0 cm on average. — duration: commonly on the plant approximately 12 days on average. — petal color when first and fully open: upper and under surfaces are commonly near White Group NN155A with a very small coloration of Green-Yellow Group 1D just at the point of attachment. — petal color at end of blooming: upper and under surfaces are commonly near White Group NN155A with no coloration at the point of attachment.

*Petal*.—Number: approximately 27 on average. — drop: good. — length: approximately 4.0 cm on average. — width: approximately 4.5 cm on average. — shape: overall shape is broadly obovate; apex is rounded to slightly cuspidate; and base is cuneate. — margin: entire with moderate undulation.

*Petaloids*.—Number: approximately 2 per flower on average. — color: commonly near White Group NN155A. — size: length is approximately 1.5 cm on average; width is approximately 5.0 mm on average.

*Stamen*.—Number: approximately 96 on average. — anthers: number is about 96; color is commonly near Yellow-Orange Group 17B; length is approximately 2.0 mm on average; shape is oval. — filaments: length is approximately 8.0 mm on average; color is commonly near Yellow Group 2C.

*Pistils*.—Arrangement: separate and free. — number: approximately 46 on average. — style: color is mostly near Yellow Group 2C; length is approximately 6.0 mm on average. — stigma: color is commonly near Yellow Group 2B; diameter is typically less than 1.0 mm; shape is fan shaped.

*Receptacle*.—Achenes stand on the bottom and wall; diameter is approximately 6.0 mm on average, depth is approximately 5.0 mm on average; shape is urn shaped; color is commonly near Yellow-Green Group 144A; surface texture is smooth.

*Pollen*.—None observed.

*Hips/seed*.—None observed.

Development:

*Vegetation*.—Semi-glossy, medium green, vigorous, and strong.

*Blooming*.—Abundant and continuous from spring through frost; typically in bloom from May to November in Southeastern Pennsylvania.

*Hardiness*.—Hardy to USDA Zone 5.

*Resistance to disease*.—Very good resistance for black spot (*Diplocarpon rosae*) and powdery mildew (*Sphaerotheca pannosa*) disease under normal greenhouse growing conditions in Cochranville, Pa.

Plants of the 'KORfloci111' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda Rose Plant characterized by the following combination of characteristics:

(a) forms attractive cup-like white colored blossoms, (b) exhibits a very bushy and rounded growth habit, (c) forms vigorous vegetation, (d) forms attractive ornamental semi-glossy, medium green foliage, and (e) exhibits very good disease resistance;

substantially as herein shown and described.

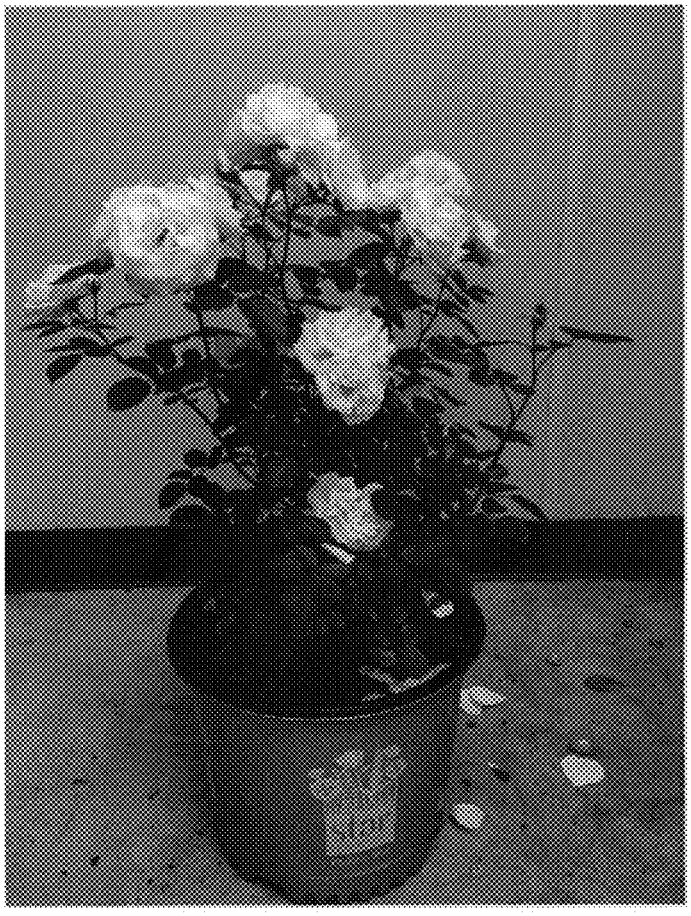

* * * * *